United States Patent [19]

Driskell

[11] Patent Number: 4,687,443
[45] Date of Patent: * Aug. 18, 1987

[54] SUBMERGIBLE POST-TYPE DENTAL IMPLANT SYSTEM AND METHOD OF USING SAME

[75] Inventor: Thomas D. Driskell, Westerville, Ohio

[73] Assignee: Boehringer Mannheim Corporation, Warsaw, Ind.

[*] Notice: The portion of the term of this patent subsequent to Oct. 15, 2002 has been disclaimed.

[21] Appl. No.: 765,064

[22] Filed: Aug. 9, 1985

Related U.S. Application Data

[63] Continuation of Ser. No. 486,903, Apr. 20, 1983, Pat. No. 4,547,157.

[51] Int. Cl.$^4$ .................................................. A61C 8/00
[52] U.S. Cl. ....................................................... 433/173
[58] Field of Search .......................... 433/173, 175, 176

[56] References Cited

U.S. PATENT DOCUMENTS 4,187,609  2/1980  Edelman ............................. 433/176
4,293,302  10/1981  Hassler et al. ...................... 433/173

Primary Examiner—Robert Peshock
Attorney, Agent, or Firm—Woodard, Weikart, Emhardt & Naughton

[57] ABSTRACT

A submergible, post-type dental implant system for anchoring an artificial crown or bridge in a row of teeth or edentulous or partially edentulous area includes a root structure which is surgically implanted transgingivally and into the bone therebeneath, an implant head which is compatibly sized and shaped to fit over an upper tapered portion of the root structure. Prior to the assembly of these two titanium alloy components, a healing cap is disposed over the tapered portion of the root structure during the time interval for healing which may be as much as three to six months. After the healing periods has ended, a tool is used to remove the healing cap and thereafter the implant head is aligned and slid over the top tapered portion of the root structure. The assembly concept employed is that of a locking taper concept where implant head retention on the root structure is dependent on the friction between the head and root of the implant generated by impacting the female taper of the implant head with its male counterpart on the root structure. The lower or inserting portion of the root structure is disposed with a series of substantially parallel fins which serve as cutting fins and generate small bone chips from particles which facilitate a "seeding" action and serve as nucleation sites for early bone formation within the various recesses and contours of this lower anchoring portion of the root structure.

19 Claims, 14 Drawing Figures

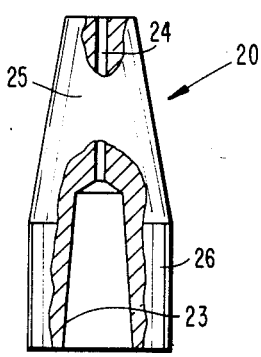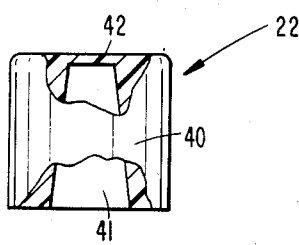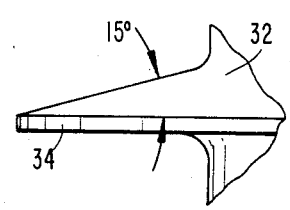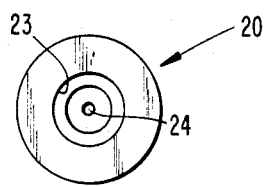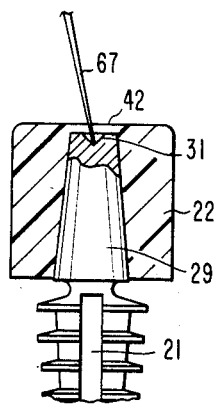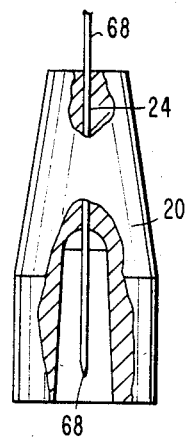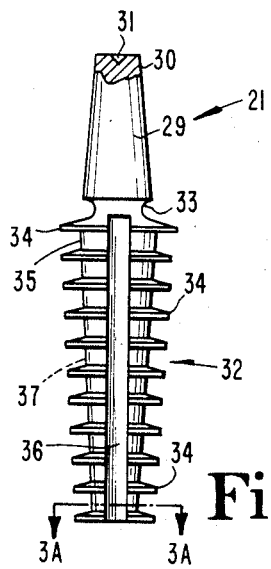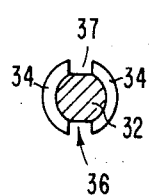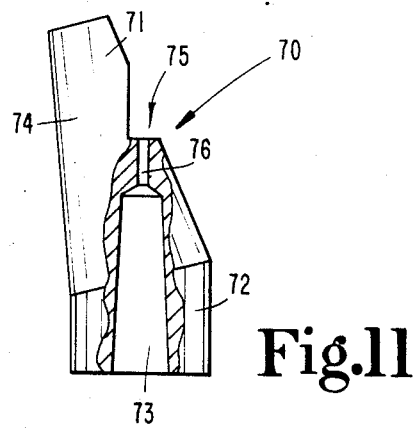

SUBMERGIBLE POST-TYPE DENTAL IMPLANT SYSTEM AND METHOD OF USING SAME

This application is a continuation of application Ser. No. 486,903, filed Apr. 20, 1983, now U.S. Pat. No. 4,546,157, issued Oct. 15, 1985.

BACKGROUND OF THE INVENTION

The concept of dental implants is well known in the art. typically an inserted member (or members) provides the support for an artifical tooth as a replacement for a natural tooth or as an abutment for bridge work. This somewhat simplistic yet very straightforward approach to the implementation of a dental implant has, over the years, been subject to numerous modifications and improvements. Many of these modifications and improvements have been necessitated by unique situations resulting from the fact that not everyone's mouth or dental array is identical. Certain types of patients have peculiarities which cannot be accommodated by the standard dental implants typically available. For these individuals and others like them, efforts have been directed at providing specialized implants and methods of installing so as to handle these unique cases.

Additionally, over the years that dental implants have been used, dentists and oral surgeons have realized certain occurrences within the tissue and bone structure of the mouth which have lead to further developments that have improved the overall level of dental care by the use of implants. One type of dental implant wherein the supporting base and the post for the crown are of a one-piece construction is disclosed by the U.S. Pat. No. 3,950,850 issued to Driskell on Apr. 20, 1976. This single-piece approach was also followed in the design presented by U.S. Pat. No. 4,302,188 issued Nov. 24, 1981 to Driskell. In each of the foregoing patent references, a great deal of attention is directed to the design of the base and ways to improve the rigidity and strength of the base for anchoring and supporting the post which ultimately receives the crown or bridge work.

One area of concern which has evolved with the use of dental implants is the growth of bone and tissue around the implant after a socket has been prepared and the implant inserted in that socket. Clearly, it is an advantage to have the tissue and bone surrounding the socket initiate regrowth as quickly as possible and that it be compatible with the dental implant material.

With a one-piece implant, the typical procedure involves anchoring the implant in the prepared socket and thereafter securing the crown or bridge to the supporting post portion of the implant. Whatever the time requirement is for this surgical procedure, the patient leaves with the crown or temporarily splinted crown or bridge in place without "wearing" just the supporting post of the implant for a period of time while the socket heals and tissue and bone growth begins. Consequently, problems may be encountered by the patient if the crown or temporarily splinted crown or bridge and its supporting implant are jarred or struck or in some manner damaged prior to full seating and healing of the implant by the tissue and bone growth. One way to avoid this particular problem is to structure the dental implant into two members, an insertion member which goes into the prepared socket and a detachable and separable post portion which attaches to the inserted portion. By this two-part construction, it is possible to anchor the inserting portion of the implant in a subgingival manner into the socket and thereafter cover it with the flaps of the gum which have been cut away in order to initially prepare the socket. This covering by the gum tissue allows the socket to be protected and heal more quickly. After a time interval when healing has adequately occurred and both tissue and bone growth has been initiated in and around the anchoring portion of the implant so as to securely anchor it in place, the covering portion of the gum can be opened and thereafter the supporting post portion of the implant attached to the inserted portion. This two-piece post-type implant arrangement presents an advantage over the single-piece units due to the healing and tissue and bone growth migration which is permitted without the presence of a post or crown extending above the gum line which is susceptible to being hit, moved, or otherwise damaged to a degree that the inserted portion of the implant might be jarred within the socket and either cause injury or damage to the socket or otherwise weaken the bone and tissue grown which has already started.

This two-piece arrangement is often referred to as having a removable head and while numerous dental implants have been developed which feature such a removable head, the prior art of which the applicant is aware includes heads which are cemented, threaded or held in place with screw fasteners. Representative of this type of an approach is the Omnii implant system offered by Omnii International, 306 East Tyler Street, Tampa, Fla. The Omnii system includes three component parts, the first being an insertion member which is designed for insertion into a prepared socket. This first member includes an internally threaded head portion which is below or flush with the gum line when this member is fully inserted into the socket. The internally threaded open end of this member may be fitted with a plug and thereafter the plug may be removed and a crown support is threadedly installed. Apparently the purpose of the plug is to keep the internally threaded opening in the insertion member free from any debris or tissue migration such that once the plug is removed, the internally threaded opening is ready for receipt of the externally threaded stem portion of the implant post which then must be installed.

One of the problems with prior art devices such as that disclosed by the Omnii implant system literature is the alignment of the head portion with the root portion which has been inserted into the socket. As should be fairly well understood, the orientation of the inserted portion will determine the orientation of the crown support post due to the fact of its threaded engagement. Consequently, it become quite critical to precisely orient, radially, the inserted portion. Secondly, in the event the threaded engagement with the plug and the inserted portion becomes too tight or in any manner binds, the torque required to remove the plug will be transmitted to the inserted portion and weaken its anchoring within the bone and tissue which has begun to grow around the various contours of this inserted portion. For these reasons, it is felt that the type of device disclosed by the Omnii International publication entitled "Omnii Implant Systems" is really not as suitable as the present invention for an effective and reliable two-piece, post-type implant system.

The present invention, however, employs a locking taper concept where the head retention is dependent on the friction between the head and the root of the implant which is generated by impacting the female taper of the head with its male counterpart in the root portion. This method of attachment is believed to be preferred over the prior art devices, and alignment of the head portion with the root portion is easily made. Due to the conical nature of the tapered fit, the head portion which assembles to the inserted portion may be oriented in any manner desired at the time of making this assembly and is not in any way dependent on the orientation of the inserted portion.

By the use of a healing cap during the critical protected, unloaded healing phase, the present invention enables the root structure implant to securely anchor into its prepared socket. Further, the healing cap is dimensionally equivalent to the base of subgingival portion of the head. Its function in addition to isolating and protecting the healing root structure from trauma, is to form a new sulcus so that the implant head will fit perfectly when permanently placed 3-6 months later.

The present invention provides other advantages in that the present invention is specifically designed for patients with extensive edentulous areas, grafted areas, or other sites where adequate stabilization of the implant during the critical or early healing stage might be impractical or severely compromised. When the head and root structure of the present invention are asembled and lightly tapped together, they become in effect a single unit with the equivalent strength of a one-piece implant of the same dimensions.

A further advantage of the present invention not found in any of the prior art devices is the interchangeability of any size head either straight or angled with any size root structure and this permits adaptability of the present implants to sites with anatomical anomalies to a degree not previously possible. One example of the advantage of this flexibility would be in an upper lateral site where impinging adjacent roots may require the use of a root structure of minimal diameter while aesthetics would be improved with a head of, for example, 2 mm greater diameter. Another example of this advantage provided by the present invention would where a large diameter bridge abutment of substantial load-bearing abilities needed, but the requirements of the restoration suggest incorporation of a smaller diameter head. With the present invention, one has total flexibility using interchangeable standard components. The quick, precise surgical technique enabled by the present invention is unique and unobvious and not anticipated nor rendered obvious by any of the prior art relating to dental implants.

SUMMARY OF THE INVENTION

A submergible, post-type dental implant system for support and securement of a dental prosthesis according to one embodiment of the present invention comprises an implant head for use in replacement of a natural tooth by an artificial tooth, a removable healing cap for use in preparing the surrounding sulcus and crestal bone prior to installing the implant head, and a root structure having a first end adapted for securely seating within a socket and a second opposite end suitably configured for first receipt of the healing cap and thereafter subsequent receipt of the implant head.

One object of the present invention is to provide an improved post-type, two-part dental implant system.

Related objects and advantages of the present invention will be apparent from the following description.

BRIEF DESCRIPTION OF THE DRAWINGS

FIG. 1 is a fragmentary, front elevation view of an implant head for use in replacement of a natural bone comprising a portion of and according to a typical embodiment of the present invention.

FIG. 2 is a bottom plan view of the FIG. 1 implant head.

FIG. 3 is a fragmentary, front elevation view of a root structure comprising a portion of and according to a typical embodiment of the present invention.

FIG. 3A is a section view taken along line 3A—3A in FIG. 3 as viewed in the direction of the arrows.

FIG. 4 is a fragmentary, front elevation view of a healing cap comprising a portion of and according to a typical embodiment of the present invention.

FIG. 5 is a partial front elevation view of one cutting blade of the FIG. 3 root structure.

FIG. 9 is a front elevation view in full section of the healing cap applied to the tapered post portion of the FIG. 3 root structure and including a pointed tool for removal of the healing cap.

FIG. 10 is a front elevation view in full section of a guide needle employed in combination with the FIG. 1 implant head for alignment of the head as it is applied to the tapered post portion of the FIG. 3 root structure.

FIG. 11 is a fragmentary, front elevation view of an angled implant head according to a typical embodiment of the present invention.

DESCRIPTION OF THE PREFERRED EMBODIMENT

Figure 6:
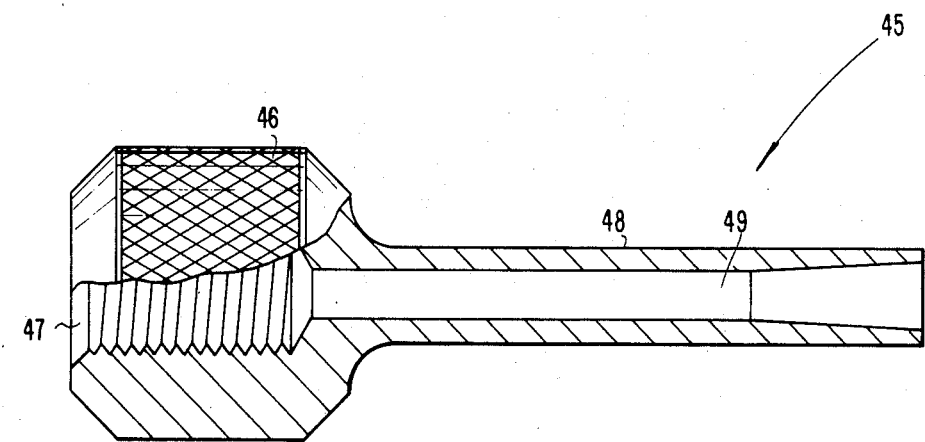
FIG. 6 is a front elevation view of an implant inserter usable with the present invention for insertion of the FIG. 3 root structure.

For the purposes of promoting an understanding of the principles of the invention, reference will now be made to the embodiment illustrated in the drawings and specific language will be used to describe the same. it will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIGS. 1, 2, 3, 3A and 4, there is illustrated the three primary components of a submergible, post-type dental implant system according to the present invention whose final configuration with a crown applied is illustrated in FIGS. 3 and 3A. The implant head 20 is illustrated in FIG. 1, while the root structure 21 is illustrated in FIG. 3 and the third component, the healing cap 22, is illustrated in FIG. 4. FIG. 2 is a bottom plan view of the implant head 20 illustrating its generally circular and conical nature and the presence of a conical taper 23 and a smaller diameter clearance hole 24 which is aligned concentrically with the conical taper as well as the outer surfaces of the implant head. The implant head is arranged into two portions, the outer top tapered portion 25 (crown support post) and the lower or base portion 26. Base portion 26 is substantially cylindrical surface while top portion 25 is tapered throughout its entire length and has a size and contour which virtually identically matches the tapered portion of root structure 21 as will be described hereinafter.

Root structure 21 includes a top tapered portion 29 which is substantially circular in lateral cross-section throughout its length terminating at its outermost end 30 with a countersunk portion 31. The top tapered portion 29 is integral with the insertion or anchoring portion 32 and the junction between the two portions is configured with an undercut and internally radiused surface 33. The anchoring portion 32 includes a plurality of uniformly configured and spaced fins 34 which are separated by an internally radiused and undercut portion 35, and while the fins appear to extend uniformly around the body of the anchoring portion, there are vertical relief channels 36 and 37 which are cut on both sides disrupting the otherwise circular appearance of the fins from an end view orientation. With some larger root structures, more than two vertical channels may be preferred. The fins are of varying diameter size and arranged in a tapering series. An alternative configuration involves the use of a generally cylindrical array of fins rather than a tapered array as illustrated. All other aspects of this alternative configuration are the same as described for root structure 21. As should be understood, each of the individual fins would be of full circular shape and concentric orientation, but for the presence of vertical channels 36 and 37 which are substantially and diametrically opposite to one another. The channels in effect split the tapering series of fins into two series, one on each side of the anchoring portion. Each fin 34 while being substantially flat on its undersurface does have an incline across its upper surface as is most effectively illustrated in FIG. 5. The two channels 36 and 37 are illustrated in FIG. 3A and while only a single fin 34 has been shown, the remaining fins which are stacked above the illustrated fin are similar in contour, though larger in outside diameter and sequentially stacked so as to provide an overall tapered appearance for anchoring portion 32.

Referring to FIG. 4, healing cap 22 which is constructed of a flexible, silicone rubber compound is illustrated and includes a generally cylindrical body portion 40 and an interior though blind and tapered recess 41. The diameter size, taper and configuration of recess 41 is substantially the same as that of top tapered portion 29 and that of conical taper recess 23. In fact, the healing cap is in essence a foreshortened implant head and is fitted on the root structure in order to simulate the subgingival contour of the head during the healing period. The similarity between these three component parts as to the diameter size and general contour of their conical tapered portions is important to the overall method and functioning of the implant system as will be apparent from the various descriptions which follow. As should be understood, healing cap 22 is completely closed at its outermost end by a relatively thin membrane 42 which encloses the smaller diameter end of the tapered recess 41.

Figure 6A:
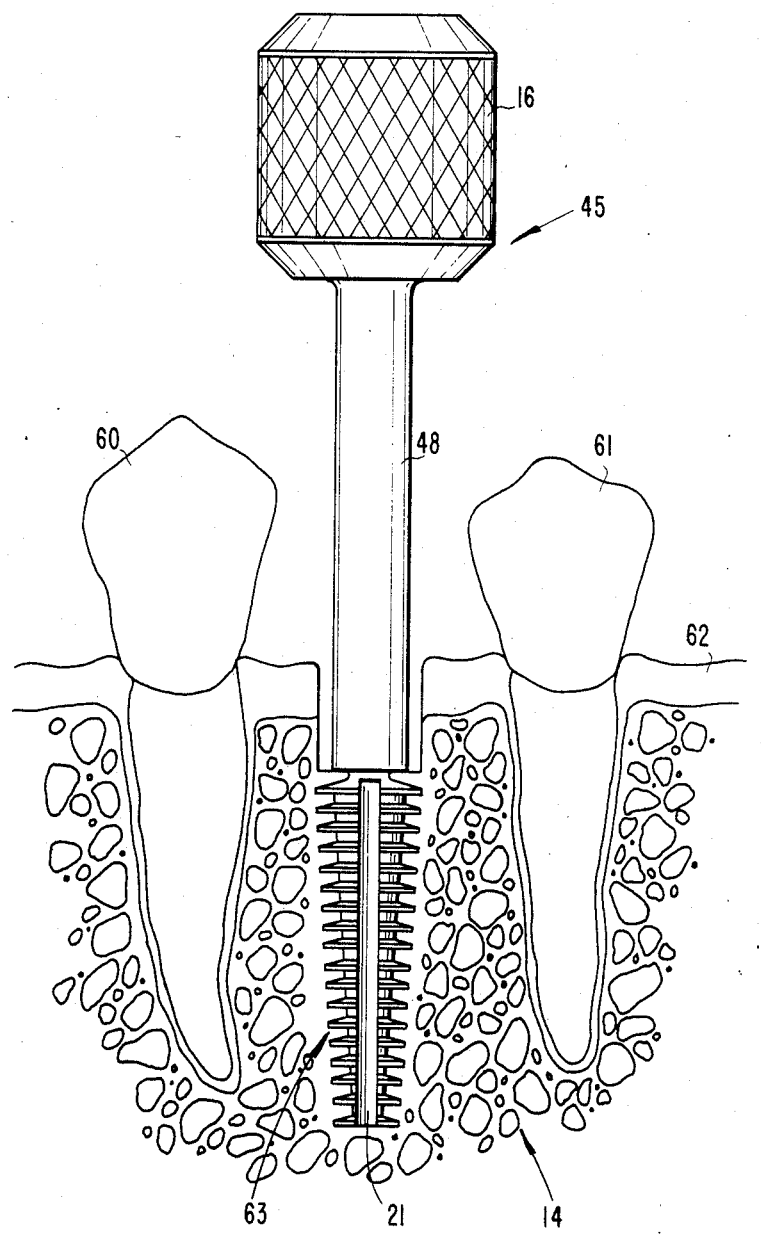
FIG. 6A is a front elevation schematic view of the FIG. 6 inserter as positioned on the FIG. 3 root structure.

Referring to FIG. 6, there is illustrated an implant inserter 45 which includes a knurled head portion 46 which is internally threaded at 47 and extending outwardly from the head in a substantially concentric manner is stem portion 48. Internal to stem portion 48 is a slightly tapered clearance bore 49 which extends the full length of the stem portion and opens into the clearance area provided by the internal threaded area 47. The implant inserter 45 is used in connection with the root structure of the subject dental implant system as will be described hereinafter. FIG. 6A illustrates the attachment of the inserter 45 to root structure 21.

Figure 7:
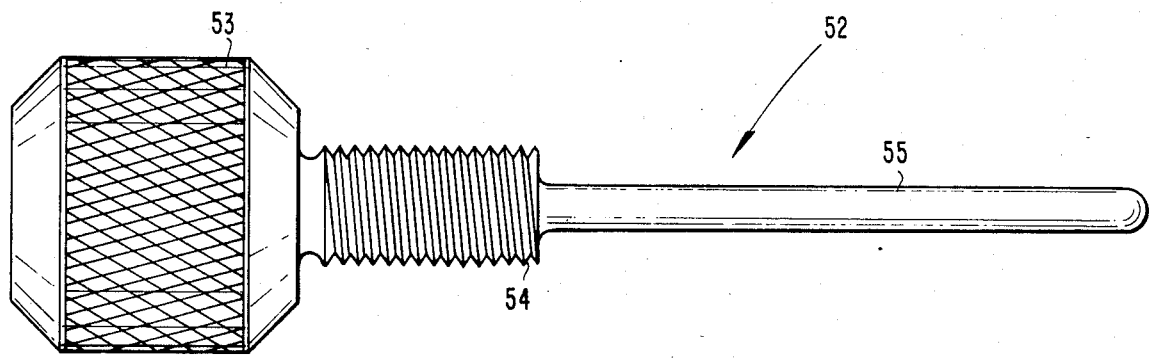
FIG. 7 is a front elevation view of an implant inserter ejector pin usable in combination with the FIG. 6 implant inserter for removal from the FIG. 3 root structure after installation.
Figure 7A:
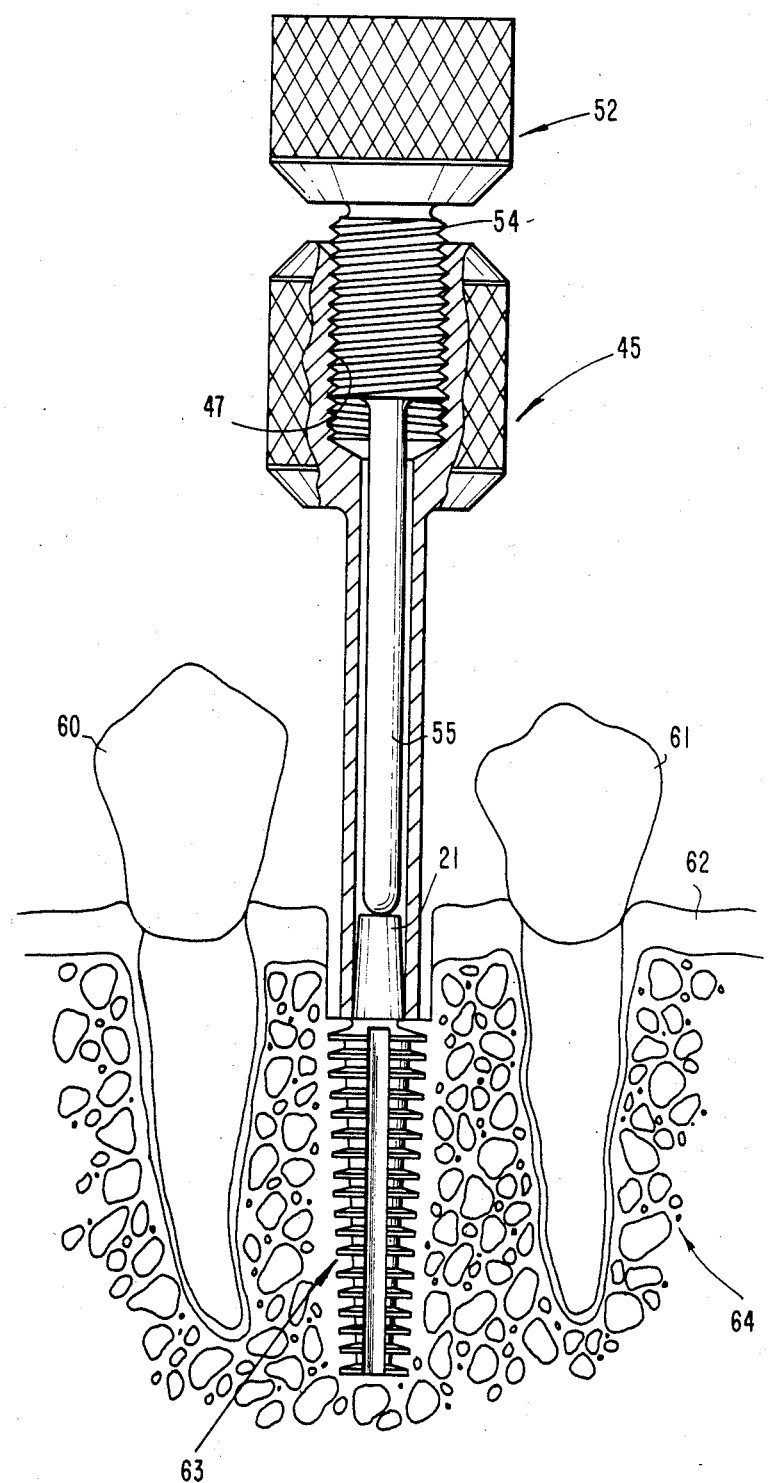
FIG. 7A is a front elevation schematic view of the FIG. 7 ejector pin as assembled to the FIG. 6 inserter.

Referring to FIG. 7, an implant ejector pin 52 is illustrated and includes a knurled head portion 53 and outwardly extending therefrom a threaded shank portion 54 and outwardly extending from that a smaller pin portion 55. Pin portion 55 and shank 54 and knurled head 53 while being of different diameters are nevertheless concentrically oriented one with respect to the other on a common axis which is central to ejector pin 52. This tool operates in combination with the implant inserter 45 and the usage of the ejector pin will be disclosed hereinafter. FIG. 7A illustrates the assembly of the ejector pin to the inserter 45.

Figure 8:
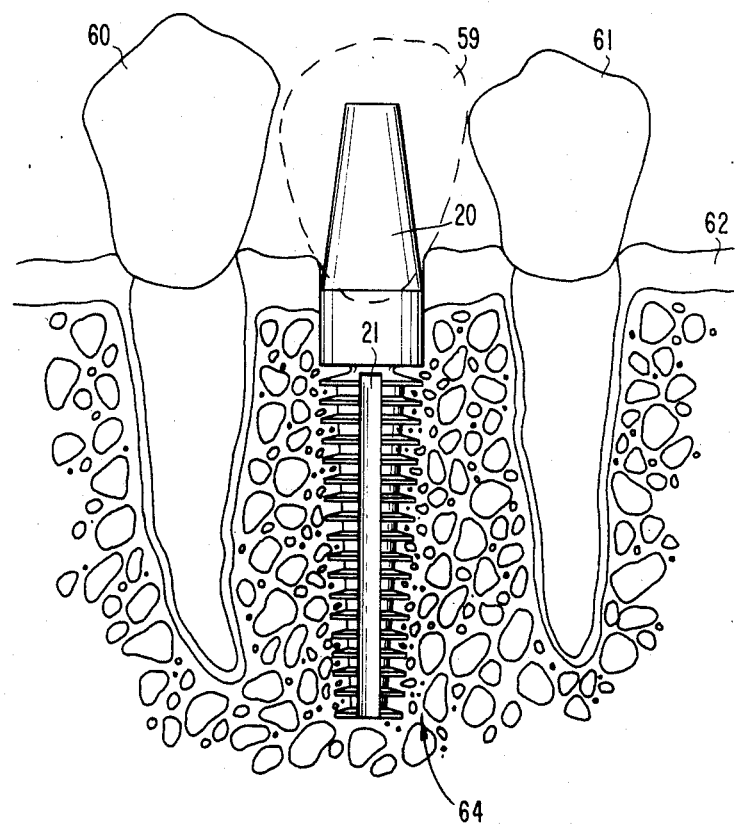
FIG. 8 is a partial front elevation view in full section of the dental implant according to the present invention as installed in the jaw and fully anchored and having received thereon an artifical crown.

Referring to FIG. 8, the finished implant is illustrated in full section and includes root structure 21 and secured thereto implant head 20 onto which a crown 59 has been placed. This implant has been disposed between two natural teeth 60 and 61 and properly positioned along the gum line 62. As is illustrated, the anchoring portion 32 of the root structure 21 has been inserted into a prepared socket 63 which extends through the gum line and into the bone 64 therebeneath.

FIG. 9 relates to the method of removal of the healing cap 22 from the top tapered portion 29 of root structure 21. The procedure involves insertion of a pointed tool 67 through membrane 42 and into the countersunk area 31. From that point, the pointed tool is tilted while a lifting or prying action is exerted thereby separating the healing cap 22 from the top tapered portion 29. FIG. 10 illustrates one method for installing the implant head 20 over the top tapered portion 29 of root structure 21. The procedure involves threading the implant head 20 over a relatively small diameter syringe needle 68 by way of clearance hole 24. Due to the compatibly sized diameters of clearance hole 24 and syringe needle 68, it is possible to use the syringe needle as a guide in order to place the implant head properly and securely onto the top tapered portion 29 of the root structure. The use of a syringe needle also enables the flushing of the interface with sterile saline solution so as to purge the male and female junction of any contaminant or other debris prior to mating together.

FIG. 11 provides one option to the straight design of implant head 20 by enabling an angled head 70 whose design and purpose are similar to head 20 except for the fact that the tapered upper portion 71 is inclined relative to the lower base portion 72. Female taper 73 is sized and shaped so as to be compatible with the locking taper concept of the present invention. While surface 74 is otherwise inclined, it does have a notch 75 disposed across opening 76 which is concentric with taper 73. This notch provides a flat striking surface for use when installing the head onto the root structure.

The procedure for installing and using the submergible, post-type dental implant system of the present invention involves a plurality of preparation and assembly steps. The procedure begins with the examination and preparation of the patient. The location for the implant must be examined and measured so that a suitably sized implant and a proper angle of insertion and orientation may be determined. One of the benefits afforded by the present invention is that virtually any style of implant head is usable with the same or standard root structure. Consequently, so long as the tapered conical portion which mates with the top tapered portion 29 of the root structure is provided within the interior of the implant head, a variety of head styles may be selected for use with the standard root structure. As previously described, FIG. 11 illustrates one such alternative wherein the implant head is actually angled and this may be employed in circumstances such as for the lateral incisor area in order to obtain maximum usage of the available alveolar bone which is in this area. Other implant head alternatives and modifications are also envisioned, although the lengthy list of options does not enable disclosure of all as part of this application, it is important to understand that the implant heads are interchangeable and fully compatible with the disclosed root structure so long as the conical taper is provided in the base portion of the implant head.

The next step in the procedure after locating the proper configuration for the root structure and proper selection of the implant head is to prepare the socket which will receive the anchoring portion 32 of the root structure. This begins by preparation of the patient and the surgical site using the standard and accepted techniques. An incision is made along the crest of the alveolar ridge to the bone and the incision is made long enough to allow for adequate reflection without tearing the tissue. Next, using a periosteal elevator, the surgeon reflects the mucoperiosteal tissue on both the buccal and lingual sides. The flaps are to be reflected to expose the alveolar ridge completely. At this point in the procedure, the surgeon removes any existing tissue tags in order to aid proper healing and retractors or sutures are used to maintain the reflected mucoperiosteal tissue well away from the surgical area. At this point, preparation of the socket which will ultimately receive the anchoring portion of the root structure is inititaed by drilling and reaming to the proper depth and diameter. It is important during this procedural step to maintain proper alignment and depth with the drilling and reaming procedure. The depth is determined by the location of the undercut and internally radiused surface 33 of the root structure which sould be disposed approximately 2 mm below the crest of the alveolar ridge. Radiographs of the pilot drill in position may be used to determine the alignment and depth of the initial hole for preparation of the socket. This initial hole then is enlarged and tapered by subsequent drilling and reaming operations. With the present invention, there are in effect two options for the procedure to be followed with respect to the final reaming and reamer sizes. The first option involves using a reamer to prepare the socket to the final size. When following this method, the reamer must be removed frequently in order to clear bone cuttings from the flutes of the reamer. Again, a radiograph may be taken with the reamer in position in order to assure proper alignment and depth. With the final socket now to size, the next step is to select the desired root structure 21 for the implant location and attach it to implant inserter 45. This attachment is made by mating the top tapered portion 29 of the selected root structure with the clearance bore 49 of the implant inserter. Slight finger pressure will firmly connect the two components together and thereafter by grasping the knurled head portion 46 of the implant inserter, the selected root structure 21 is inserted into the prepared socket as far as it will go. Then, while exerting pressure apically, the implant inserter is rotated between the thumb and forefinger (by grasping the knurled head portion). So long as moderate pressure is applied apically, the connection between the top tapered portion 29 and clearance bore 49 will not slip. Vertical channels 36 and 37 have sharp outer edges and thus the root structure is firmly seated without the necessity of more than a slight tap of a mallet.

Although the socket was prepared more or less to its final size, the method of insertion of the root structure involves some rotation and the presence of fins 34 act as cutting members as do the vertical channels 36 and 37. The cutting action of these portions of the root structure result in fine particles of autogenous bone being disposed within the vertical channels and in between the various horizontal fins of the anchoring portion 32. These small particles of bones or bone chips which are viable and osteogenic act as nucleation sites for early bone formation within the spaces and recess of the root structure thus speeding up the healing process.

As an alternative to this foregoing procedure regarding the initial implanting of the root structure into the prepared socket, it is possible with the present invention to omit the final reamer sizing step and allow the selected root structure to do the final sizing itself. When this method is employed, the preparation of the socket stops with a smaller reamer size and there is a greater force and torque requirement on the root structure in order to seat it into what is now a smaller prepared socket size. This installation of the root structure is still performed by the implant inserter 45, but as indicated, a slightly greater force will be required due to the smaller size and the greater dimension of bone and tissue which must be cut through in order to get full seating of the root structure within the bone and tissue. A third alternative to this procedure is to use the final full-diameter reamer size but not to insert it as fully in to the depth of the socket as before and thereafter allow the selected root structure to do the final sizing.

By whatever method is selected, once the selected root structure is firmly seated, the implant inserter 45 may be removed by use of the implant inserter ejector pin 52. Pin portion 55 of the ejector pin is inserted through the top portion of the implant inserter (through internally threaded portion 47) and thereafter through clearance bore 49 until such time as threaded shank 54 engages the internally threaded portion 47. These two portions are threaded together and as this threading action occurs, the pin portion comes in contact with the top surface of the top taper portion 29 thereafter releasing the implanted inserter 45 from the root structure.

With the root structure properly implanted, the coronal tip of the root structure top tapered portion 29 whould be about even with or slightly above the crest of the ridge. The insertion site is then flushed thoroughly with saline and the healing cap is then seated on the top tapered portion 29. The healing cap 22 is seated as far as it will go and this step is important since the healing cap will determine the shape of the sulcus and the contour of the crestal bone during the period of time that healing is occurring. Although the healing period may be from three to six months, certain indications are that the time period may be shorter. It is important to note that the healing cap 22 has a shape and contour which is substantially the same as bottom portion 26 of the implant head. Consequently, healing cap 22 serves as a temporary simulation of the bottom portion which will ultimately be placed in that position as part of the final implant procedure. Consequently, since it is the size, shape and location of the healing cap which determines the shape of the sulcus and the contour of the crestal bone, once those items are adapted to the shape of the healing cap, a smooth and proper fit of the implant head is virtually guaranteed. After the healing cap is in place, the tissue flaps are then closed and sutured over the cap in order to both protect and enhance healing during the healing period.

After a suitable healing period has elapsed, it is then time to remove the healing cap and install the implant head. Examination of the site will reveal whether or not the healing cap is slightly exposed. If the cap is completely exposed, a periodontal probe or similar sharp-pointed instrument such as pointed tool 67 is inserted through the top surface membrane 42 of the healign cap and into the coutnersunk area 31 of the root structure. Once contact is made with the countersunk surface, the pointed tool is angled and lifted so that the point can actually lift the healing cap up and away from the top tapered portion 29. If gingival tissue is covering or partially covering the healing cap, then the desired margin should be contoured by the dentist prior to attempting to expose the top tapered portion 29. Examination of the implant site will reveal a well-shaped and healed space around the top tapered portion 29 ready for final placement of the implant head 20. The implant site should be flushed with sterile saline solution due to the fact that bleeding will probably have occurred. A small syringe filled with sterile saline and fitted with a needle is then inserted into the small irrigation port in the top of the implant head 20 and into clearance hole 24 as previously illustrated in FIG. 10. The syringe needle 68 extends completely through the head and is placed vertically on the countersunk portion 31 of the root structure. The implant head is then slid down the needle and onto the top tapered portion 29. Sterile saline solution from the syringe is simultaneously and slowly flushed through the needle so that the implant sulcus area is continuously flushed to remove blood or other debris from the sulcus as the head is seated. It is not necessary to apply force on the implant head at this point since it might be necessary to remove the head again for further site preparation. One of the novel features of the present invention and the use of syringe needle 68 both as a guide and as a cleansing agent for the implant site is that a forcible squirt of saline from the syringe into the needle hole with the needle inserted into the head as far as it will go will pop off the implant head from the top tapered portion allowing it to be reseated after further site preparation if necessary. With the angled-head design of FIG. 11, it is to be noted that the notched area serves a dual function. First of all, it provides a flat surface for initial alignment of the syringe needle 68 but secondly and possibly more importantly provides a flat surface for which impact on the head may be made using a mallet or similar nstrument. With the angled implant head of FIG. 11 as opposed to the straight head of FIG. 1, care should be taken to properly rotate and orient the angled head prior to impact which will undoubtedly seat the implant head securely on the top tapered portion of the root structure.

As has been previously described, the present invention employs a locking taper concept where implant head retention is dependent on the friction between the head and root structure of the implant generated by impacting the female taper of the head with its male counterpart on the root portion. As stated, one objective of the present invention is that all head designs will mate with all root designs interchangeably if the locking taper dimensions are equal. However, it may be desirable to adjust these dimension from, for example, the smallest implant size to the largest implant size so that in reality two or more families of interchangeable heads and roots might exist based on two or more sizes of mating locking tapers. Another advantage of interchangeability is that one size of root might be used because of the available bone or spacing of adjacent tooth roots and mated with another size of head in order to improve the aesthetics of the crown at the gingival margin.

As the root portion incorporates the male locking taper, a healing cap, in essence, a foreshortened head is fitted on the root to simulate the subgingival contour of the head during the healing period which may be as much as three to six months. This healing cap not only forms the subgingival and alveolar crestal contours, but it also protects the surface integrity of the male locking taper while permitting passive healing of the root.

The implant head which contains the female locking taper has a smaller-diameter relief hole extending through from the female taper to the upper face of the implant head. This relief hole, as previously noted fulfills three primary functions. The first is to engage a snugly-fitting syringe needle 68 which is inserted though the bore and is attached to a sterile water or saline-filled syringe in order to facilitate flushing the male and female locking taper components as they are being mated and, in the case of an angulated head, rotationally aligned. This process flushes out any blood, tissue particle sor other extraneous material which might interfere with the precision fit of the locking taper components. This relief hole (clearance hole 24) also acts as a pressure-relief port precluding the possibility of a pressure head forming when the male component is inserted into the female component of the locking taper mechanism. The final primary function is that the relief hole functions as an access port to the coronal face of the male locking taper component thus permitting the insertion of a rod extension of a miniature wheel puller screw jack if removal of the implant head is required subsequent to seating and impaction.

The material employed for the implant head and root structure is a titanium alloy machined to very fine tolerances and smooth surface finish. While this material is believed preferred due to its material properties and inert behavior relative to the tissue and bone with which it interfaces, other similar materials may also be utilized according to the teachings of the present invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A submergible, post-type system for use in combination with an artificial dental element for implanting said artificial dental element into the bone structure of a human jaw, said system comprising:
    an anchoring root member having a first end adapted for securely seating within said bone structure, and a second, opposite receiving end;
    a temporary healing cap adapted to be received by said receiving end during healing of said bone structure around the first end of said anchoring root member; and
    an implant head adapted to receive said artificial dental element and being receivable by said receiving end after removal of said temporary healing cap, said implant head having a subgingival base portion the size and shape of which is simulated by said temporary healing cap.

2. The dental implant system of claim 1 wherein said first end includes a plurality of fins of varying sizes arranged into a tapering series.

3. The dental implant system of claim 2 wherein said first end further includes at least one channel oriented to break continuity of said plurality of fins.

4. The dental implant system of claim 1 wherein said second, opposite receiving end includes a tapered receiving portion having a substantially circular lateral cross section.

5. The dental implant system of claim 4 wherein said implant head includes an artificial dental element support post portion adjacent a first end and a tapered received portion adjacent an opposite end, said tapered receiving and received portions being substantially the same in size and shape.

6. The dental implant system of claim 1 wherein said implant head includes an artificial dental element support post portion adjacent a first end and a tapered received portion adjacent an opposite end.

7. The dental implant system of claim 6 wherein said artificial dental element support post portion and said tapered received portion are generally concentric to each other.

8. The dental implant system of claim 6 wherein said artificial dental element support post portion is inclined relative to said tapered received portion.

9. The dental implant system of claim 6 wherein said healing cap has a generally cylindrical body portion and a tapered receiving portion which is substantially identical in size and shape to the tapered received portion of said implant head.

10. The dental implant system of claim 6 wherein said implant head further includes a clearance hole which extends through said implant head and is disposed substantially concentric to said tapered received portion.

11. The dental implant system of claim 1 wherein said healing cap has a generally cylindrical body portion and a tapered received portion disposed within said body portion.

12. A submergible, post-type system for use in combination with an artificial dental element for implanting said artificial dental element into the bone structure of a human jaw, said system comprising:
    an interchangeable anchoring root member having a first end adapted for securely seating within said bone structure, and a second, opposite receiving end;
    a temporary healing cap adapted to be recieved by said receiving end during healing of said bone structure around the first end of said anchoring root member; and
    an interchangeable implant head adapted to receive said artificial dental element and being receivable by said receiving end after removal of said temporary healing cap, said implant head having a subgingival base portion the size and shape of which is simulated by said temporary healing cap.

13. The dental implant system of claim 12 wherein said first end includes a plurality of fins of varying sizes arranged into a tapering series.

14. The dental implant system of claim 13 wherein said first end further includes two oppositely disposed vertical channels oriented to segment said plurality of fins into two fin series, one on each side of each vertical channel.

15. The dental implant system of claim 13 wherein said second, opposite receiving end includes a tapered portion having a substantially circular lateral cross section.

16. The dental implant system of claim 15 wherein said tapered portion tapers in a direction opposite to the direction of taper of said tapering series of fins.

17. The dental implant system of claim 12 wherein said implant head includes an artificial dental element support post portion adjacent a first end and a tapered received portion adjacent an opposite end.

18. The dental implant system of claim 17 wherein said artificial dental element support post portion and said tapered received portion are generally concentric to each other.

19. The dental implant system of claim 17 wherein said artificial dental element support post portion is inclined relative to said tapered received portion.

* * * * *